United States Patent
Boaz

(10) Patent No.: US 9,469,595 B1
(45) Date of Patent: Oct. 18, 2016

(54) REDUCTIVE AMINATION OF NITRILES USING TRANSFER HYDROGENATION

(71) Applicant: Eastman Chemical Company, Kingsport, TN (US)

(72) Inventor: Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/745,506

(22) Filed: Jun. 22, 2015

(51) Int. Cl.
*C07C 209/48* (2006.01)
*C07C 213/02* (2006.01)

(52) U.S. Cl.
CPC ............ *C07C 209/48* (2013.01); *C07C 213/02* (2013.01)

(58) Field of Classification Search
CPC ..................... C07C 209/48; C07C 213/02
See application file for complete search history.

(56) References Cited

U.S. PATENT DOCUMENTS

| | | | |
|---|---|---|---|
| 5,237,088 A | 8/1993 | Weigert | |
| 5,463,130 A | 10/1995 | Witzel et al. | |
| 5,869,653 A | 2/1999 | Johnson | |
| 5,894,074 A | 4/1999 | Fuchs et al. | |
| 7,709,655 B2 * | 5/2010 | Zhang ................. | C07F 15/0066 548/250 |
| 9,139,511 B2 * | 9/2015 | Wigbers et al. ...... | C07C 209/48 |

FOREIGN PATENT DOCUMENTS

WO WO 2013/169401 * 11/2013

OTHER PUBLICATIONS

Yap et al. Organometallics, 33(4), 930-940, 2014.*
Stutz et al, J. Med. Chem., 1986, 29(1), 112-25.*
Chen et al.; "Hydrogen transfer reduction of nitriles in DBU based ionic liquids"; ARKIVOC; 2012; (viii); pp. 128-136.
Gowda et al.; "Application of hydrazinium monoformate as new hydrogen donor with Raney nickel: a facile reduction of nitro and nitrile moieties"; Tetrahedron; 58; (2002); pp. 2211-2213.
Mebane et al.; "Transfer Hydrogenation of Nitriles with 2-Propanol and Raney® Nickel"; Synthetic Communications: An International Journal for Rapid Communication of Synthetic Organic Chemistry; vol. 33, No. 19, pp. 3373-3379, 2003.
Moiseev et al.; "Facile hydrogen-transfer reduction of multiple bonds by formic acid catalyzed with a Pd-561 giant cluster"; Mendeleev Commun.; 1997; 7(1); pp. 1-3.
Shares et al.; "An efficient synthesis of tertiary amines from nitriles in aprotic solvents"; Tetrahedron Letters; 53(2012); pp. 4426-4428.
Copending U.S. Appl. No. 14/745,508, filed Jun. 22, 2015, Neil Warren Boaz.

* cited by examiner

*Primary Examiner* — Shailendra Kumar
(74) *Attorney, Agent, or Firm* — Kenrick L. Vidale

(57) ABSTRACT

This disclosure describes a low temperature process for the preparation of tertiary amines from nitriles and secondary amines via reductive amination using transfer hydrogenation. The process can use a nitrile and a dialkylamine and proceeds under surprisingly mild conditions using a palladium catalyst and the corresponding dialkylammonium formate as the hydrogen donor, and show a pronounced acceleration in the presence of water.

12 Claims, No Drawings

REDUCTIVE AMINATION OF NITRILES USING TRANSFER HYDROGENATION

BACKGROUND

Reductive amination of nitriles using dihydrogen in the presence of a secondary amine is a known process for preparing tertiary amines from nitriles. These reductions are generally run at high temperatures and high hydrogen pressures, and often result in poor selectivity, low conversions, or high secondary amine loading. The preparation of dimethyl tertiary amines by the reduction of aliphatic nitriles with heterogeneous catalysts has been explored. These reactions generally use liquid (anhydrous) dimethylamine and are performed at high temperatures (at or above 120° C.) and high pressures (80-200 bar or 8-20 MPa). The catalysts for these reductions are usually either palladium on a support or Raney nickel.

Transfer hydrogenation is a well-known process for the reduction of unsaturated substrates that traces its roots to the classical Meerwein-Pondorf-Verley reduction. This process can avoid the hazards inherent in the use of hydrogen gas and the costs of operating at high pressure. Modern transfer hydrogenation generally utilizes a transition metal catalyst under mild conditions (temperatures below 100° C.) with a hydrogen donor molecule such as isopropanol, cyclohexene, cyclohexadiene, formic acid, formic acid salts, hydrazine, hydrazine salts, and amines. Transfer hydrogenation is most often used to reduce functionalities such as olefins, ketones, and nitro groups. Transfer hydrogenation of nitriles is known to selectively affording the corresponding primary amine as the major product, although proper choice of conditions can lead to the corresponding tertiary amine where the groups on nitrogen all derive from the nitrile. These reductions utilize either Raney nickel, palladium on carbon, or palladium clusters with a variety of hydrogen donors (isopropanol, ammonium formate, potassium formate, hydrazinium monoformate) in solvents varying from isopropanol (donor and solvent), methanol, ionic liquids, and aprotic solvents such as hexane or tetrahydrofuran. The reduction of a nitrile in the presence of a primary amine using Raney nickel catalyst has been reported. This reaction does not process via reductive amination but rather via disproportionation with the amine functioning as the hydrogen donor. Thus the reaction of a nitrile A and primary amine B under these conditions affords the alternative primary amine A and nitrile B. The reductive amination of nitriles with secondary amines using transfer hydrogenation to afford the corresponding tertiary amine has not been reported.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

There is now provided a method of the preparation of tertiary amines via reductive amination of nitriles with secondary amines using transfer hydrogenation. The method can be carried out in the presence of at least one catalyst, at least one secondary amine, and at least one hydrogen donor. The method can be carried out at an atmospheric pressure.

DETAILED DESCRIPTION

This disclosure describes a mild method for preparation of tertiary amines by reductive amination of nitriles with secondary amines using transfer hydrogenation. The method described herein would be of general use, as it would use less energy (lower reaction temperatures), avoid the hazards of hydrogen gas, require less expensive (non-pressure) reaction vessels, and/or avoid decomposition issues that are often prevalent at high temperatures.

There is provided a method for the preparation of tertiary amines represented by the general formula 1 by the transfer reductive amination of nitriles represented by general formula 2:

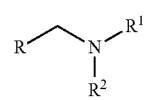

$$R-CN \quad\quad 2$$

wherein R, $R^1$, and $R^2$ are selected from substituted and unsubstituted, branched- and straight-chain $C_1$-$C_{22}$ alkyl, substituted and unsubstituted $C_3$-$C_8$ cycloalkyl, substituted and unsubstituted $C_6$-$C_{20}$ carbocyclic aryl, and substituted and unsubstituted $C_1$-$C_{20}$ heterocyclic wherein the heteroatoms are selected from sulfur, nitrogen, and oxygen, or mixtures thereof, wherein the transfer reductive amination is carried out in the presence of a catalyst, a secondary amine, and a hydrogen donor.

The branched- and straight-chain $C_1$-$C_{22}$ alkyl groups which may be represented by R, $R^1$, and $R^2$ may be straight- or branched-chain hydrocarbon radicals containing up to about 22 carbon atoms and may be substituted, for example, with one to three groups selected from $C_1$-$C_6$ alkoxy, $C_2$-$C_6$ alkoxycarbonyl, $C_2$-$C_6$ alkanoyloxy, hydroxy, carbocyclic aryl, and heterocyclic. The terms "$C_1$-$C_6$ alkoxy", "$C_2$-$C_6$ alkoxycarbonyl", and "$C_2$-$C_6$ alkanoyloxy" are used to denote radicals corresponding to the structures —$OR^3$, —$CO_2R^3$, and —$OCOR^3$, respectively, wherein $R^3$ is $C_1$-$C_6$ alkyl or substituted $C_1$-$C_6$ alkyl.

The $C_3$-$C_8$ cycloalkyl groups which may be represented by R, $R^1$, or $R^2$ may be saturated, carbocyclic hydrocarbon radicals having three to eight carbon atoms and may be substituted, for example, with one to three groups selected from $C_1$-$C_6$ alkoxy, $C_2$-$C_6$ alkoxycarbonyl, $C_2$-$C_6$ alkanoyloxy, hydroxy, $C_2$-$C_{10}$ dialkylamino, carbocyclic aryl, and heterocyclic.

The $C_6$-$C_{20}$ carbocyclic aryl groups which R, $R^1$, $R^2$, and any substituents may represent may include phenyl, naphthyl, or anthracenyl and phenyl, naphthyl, or anthracenyl substituted with one to three substituents selected from $C_1$-$C_6$ alkyl, substituted $C_1$-$C_6$ alkyl, hydroxy, $C_2$-$C_{10}$ dialkylamino, $C_6$-$C_{10}$ aryl, substituted $C_6$-$C_{10}$ aryl, $C_1$-$C_6$ alkoxy, carboxy, $C_1$-$C_6$ alkanoyloxy, $C_1$-$C_6$ alkylsulfonyl, trifluoromethyl, $C_2$-$C_6$ alkoxycarbonyl, $C_2$-$C_6$ alkanoylamino and O—$R^4$, —$SO_2$—$R^4$, —$NHSO_2R^4$ and —$NHCO_2R^4$, wherein $R^4$ is phenyl, naphthyl, or phenyl or naphthyl substituted with one to three groups selected from $C_1$-$C_6$ alkyl, $C_6$-$C_{10}$ aryl, and $C_1$-$C_6$ alkoxy.

The $C_1$-$C_{20}$ heterocyclic radicals which R, $R^1$, $R^2$, and any substituents may represent may include a 5- or 6-membered heterocyclic ring containing one to four heteroatoms selected from oxygen, sulfur and nitrogen. Examples of such heterocyclic radicals are thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heterocyclic radicals may be substituted, for example, with up to three groups such as $C_1$-$C_6$ alkyl, $C_1$-$C_6$ alkoxy, substituted $C_1$-$C_6$ alkyl, hydroxy, $C_2$-$C_{10}$ dialkylamino, aryl, aryloxy, $C_2$-$C_6$ alkoxycarbonyl, and $C_2$-$C_6$ alkanoylamino. The heterocyclic radicals also may be substituted with a fused ring system (e.g., a benzo or naphtho residue) which may be unsubstituted or substituted, for example, with up to three of the groups set forth in the preceding sentence.

The compounds of the invention are exemplified by formula 1 wherein R is a branched- and straight-chain, saturated $C_1$-$C_{22}$ alkyl, or a hydroxy-substituted branched- and straight-chain saturated $C_1$-$C_{22}$ alkyl, or a $C_6$-$C_{20}$ carbocyclic aryl or substituted carbocyclic aryl group, $R^1$ is a branched- and straight-chain, saturated $C_1$-$C_{22}$ alkyl, and $R^2$ is a branched- and straight-chain, saturated $C_1$-$C_{22}$ alkyl. The compounds of the invention are further exemplified by formula 1 wherein R is ethyl and $R^1$ and $R^2$ are the same and are each methyl, R is 2-hydroxyethyl and $R^1$ and $R^2$ are the same and are each methyl or ethyl, or R is phenyl and $R^1$ and $R^2$ are the same and are each methyl.

The method comprises the hydrogenation of nitrile 2 in the presence of a catalyst, a secondary amine, and a hydrogen donor.

The method may be carried out at a temperature between from about −100° C. to about +200° C., from about 0 to about 150° C., or from about 20 to about 100° C. The method can be carried out at a temperature less than about 150° C. or less than about 100° C.

The catalyst may be chosen from Group VIII metals. Group VIII metals may include palladium and platinum. The Group VIII metals may be on a support, which can be chosen from carbon, alumina, silica, and the like. The weight percent loading of the metal on the support can be from about 0.25% to about 20%, or from about 0.5% to about 10%, or from about 1% to about 7.5%. The amount of supported catalyst can vary from about 1 to about 50 weight percent based on the weight of substrate 2, or from about 2% to about 30%, or from about 4% to about 20%.

The amount of the secondary amine may be between about 1 to about 20 equivalents based on nitrile 2, or between about 1 to about 10 equivalents, or between about 1 to about 5 equivalents. The secondary amine can be neat or can be an aqueous solution with an amine content of between about 10% to about 90%, between about 20% to about 80%, or between about 30% to about 70%.

The hydrogen donor is a material that will effectively transfer hydrogen to the substrate. Examples of hydrogen donors may include, but are not limited to, formic acid, formic acid metal salts, formic acid ammonium salts, cyclohexene, cyclohexadiene, hydrazine, hydrazine salts, and other similar species. The hydrogen donor may be a preformed material such as cyclohexene, cyclohexadiene, or ammonium formate, or it can be formed in situ. The hydrogen donor can be formed in situ by the reaction of formic acid with the secondary amine reactant to form the dialkylammonium formate.

The amount of the hydrogen donor can be between about 1 to about 20 molar equivalents based nitrile 2, or between about 1 to about 5 equivalents, or between about 2 to about 4 equivalents.

The reaction can be performed under a variety of atmospheric or pressure conditions. For example, the reaction may be performed under air or nitrogen at atmospheric pressure.

Although not required, the presence of water in the reaction may have an accelerating effect on the reaction. The water may be introduced with a reactant and/or added directly. The amount of water can be between about 0% to about 80% of the total weight of the reaction, or between about 0% to about 60%, or between about 0% to about 40%.

The reaction may be performed in an inert solvent in addition to any solvent that may be introduced with a reagent (for example, the water content in a secondary amine aqueous solution). The solvents may include water, $C_1$-$C_6$ alcohols such as methanol, ethanol, or isopropanol, cyclic or acyclic ether solvents such as diethyl ether, diisopropyl ether, tert-butyl methyl ether, or tetrahydrofuran, aromatic hydrocarbons such as benzene, toluene, or xylene, aliphatic or alicyclic saturated hydrocarbons such as hexane, heptane, or cyclohexane, polar aprotic solvents such as acetonitrile, dimethyl formamide, or dimethyl sulfoxide, or mixtures thereof. The preferred solvents are water and/or $C_1$-$C_6$ alcohols.

The product 1 may be isolated and purified using methods known to those of skill in the art, for example, extraction, filtration, distillation and/or crystallization.

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," "contain," "including," "includes," "include," and "have" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds) and provided literal support for and includes the end points of 10 and 100.

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. These broad, intermediate, and narrow numerical ranges should be applied not only to the specific values, but should also be applied to differences between these specific values.

EXAMPLES

The processes provided by the present invention are further illustrated by the following examples:

Example 1

3-Dimethylaminopropanol

Dimethylamine (40% in water; 8.5 mL; 67.3 mmol; 4.6 equiv) was added to a 100-mL flask which was then cooled in ice-water. Formic acid (88%; 1.34 mL; 30.7 mmol; 2.1 equiv) was added with a small exotherm. The cooling bath was removed and the mixture was allowed to warm to ambient temperature. 3-Hydroxypropionitrile (1.0 mL; 14.6 mmol) was added followed by 5% palladium on carbon (42.6% in water; 470 mg; 19 wt % based on hydroxypropionitrile). The mixture was stirred at ambient temperature for 3 h, at which point a sample was analyzed by $^1$H NMR (nuclear magnetic resonance) to indicate >99.5% conversion to 3-dimethylaminopropanol.

$^1$H NMR (DMSO-$d_6$): δ 3.43 (t, 2H, J=6.40 Hz); 2.27 (t, 2H, J=7.20 Hz); 2.13 (s, 6H); 1.55 (m, 2H).

Example 2

3-Dimethylaminopropanol Using 15 wt % Catalyst

Dimethylamine (40% in water; 8.5 mL; 67.3 mmol; 4.6 equiv) was added to a 100-mL flask which was then cooled in ice-water. Formic acid (88%; 1.34 mL; 30.7 mmol; 2.1 equiv) was added with a small exotherm. The cooling bath was removed and the mixture was allowed to warm to ambient temperature. 3-Hydroxypropionitrile (1.0 mL; 14.6 mmol) was added followed by 5% palladium on carbon (42.6% in water; 366 mg; 15 wt % based on hydroxypropionitrile). The mixture was stirred at ambient temperature and samples were removed and analyzed for conversion of 3-hydroxypropionitrile to 3-dimethylaminopropanol by $^1$H NMR: 1 h, 75% conversion; 2 h, 91% conversion; 3 h, 98% conversion.

Example 3

3-Dimethylaminopropanol Using 10 wt % Catalyst

Dimethylamine (40% in water; 8.5 mL; 67.3 mmol; 4.6 equiv) was added to a 100-mL flask which was then cooled in ice-water. Formic acid (88%; 1.34 mL; 30.7 mmol; 2.1 equiv) was added with a small exotherm. The cooling bath was removed and the mixture was allowed to warm to ambient temperature. 3-Hydroxypropionitrile (1.0 mL; 14.6 mmol) was added followed by 5% palladium on carbon (42.6% in water; 235 mg; 10 wt % based on hydroxypropionitrile). The mixture was stirred at ambient temperature and samples were removed and analyzed for conversion of 3-hydroxypropionitrile to 3-dimethylaminopropanol by $^1$H NMR: 3.5 h, 45% conversion; 8.5 h, 74% conversion; 48 h, 97% conversion.

Example 4

3-Dimethylaminopropanol Using 2.5 Equiv of Dimethylamine

Dimethylamine (40% in water; 4.6 mL; 36.6 mmol; 2.5 equiv) was added to a 100-mL flask which was then cooled in ice-water. Formic acid (88%; 1.34 mL; 30.7 mmol; 2.1 equiv) was added with a small exotherm. The cooling bath was removed and the mixture was allowed to warm to ambient temperature. 3-Hydroxypropionitrile (1.0 mL; 14.6 mmol) was added followed by 5% palladium on carbon (42.6% in water; 366 mg; 15 wt % based on hydroxypropionitrile). The mixture was stirred at ambient temperature and samples were removed and analyzed for conversion of 3-hydroxypropionitrile to 3-dimethylaminopropanol by $^1$H NMR: 1 h, 97% conversion; 2 h, 99.5% conversion; 3 h, >99.5% conversion.

Example 5

3-Dimethylaminopropanol Using 1.25 Equiv of Dimethylamine

Dimethylamine (40% in water; 2.3 mL; 36.6 mmol; 1.25 equiv) was added to a 100-mL flask which was then cooled in ice-water. Formic acid (88%; 1.34 mL; 30.7 mmol; 2.1 equiv) was added with a small exotherm. The cooling bath was removed and the mixture was allowed to warm to ambient temperature. 3-Hydroxypropionitrile (1.0 mL; 14.6 mmol) was added followed by 5% palladium on carbon (42.6% in water; 366 mg; 15 wt % based on hydroxypropionitrile). The mixture was stirred at ambient temperature and samples were removed and analyzed for conversion of 3-hydroxypropionitrile to 3-dimethylaminopropanol by $^1$H NMR: 1 h, 90% conversion; 2 h, 93% conversion; 3 h, 95% conversion.

Example 6

3-Dimethylaminopropanol Using 7.5 wt % Catalyst

Dimethylamine (40% in water; 4.6 mL; 36.6 mmol; 2.5 equiv) was added to a 100-mL flask which was then cooled in ice-water. Formic acid (88%; 1.34 mL; 30.7 mmol; 2.1 equiv) was added with a small exotherm. The cooling bath was removed and the mixture was allowed to warm to ambient temperature. 3-Hydroxypropionitrile (1.0 mL; 14.6 mmol) was added followed by 5% palladium on carbon (42.6% in water; 180 mg; 7.5 wt % based on hydroxypropionitrile). The mixture was stirred at RT and samples were removed and analyzed for conversion of 3-hydroxypropionitrile to 3-dimethylaminopropanol by $^1$H NMR: 1 h, 54% conversion; 2 h, 64% conversion; 3 h, 69% conversion; 21 h, 91% conversion; 45 h, 95% conversion.

Example 7

3-Dimethylaminopropanol at Ambient Temperature with 10 wt % Catalyst

Dimethylamine (40% in water; 4.63 mL; 36.6 mmol; 2.5 equiv) was added to a flask which was then cooled in ice-water. Formic acid (88%; 1.34 mL; 30.7 mmol; 2.1 equiv) was added with a small exotherm. The cooling bath was removed and the mixture was allowed to warm to ambient temperature. 3-Hydroxypropionitrile (1.0 mL; 14.6 mmol) was added followed by 5% palladium on carbon (49.5% in water; 210 mg; 10 wt % based on hydroxypropionitrile). The mixture was stirred at ambient temperature and samples were removed and analyzed for conversion of 3-hydroxypropionitrile to 3-dimethylaminopropanol by $^1$H NMR: 1 h, 72% conversion; 2 h, 80% conversion; 3 h, 87% conversion; 4.5 h, 92% conversion; 9.5 h, 98% conversion; 24 h, >99.5% conversion, 99% selectivity to 3-dimethylaminopropanol.

Example 8

3-Dimethylaminopropanol at 50° C. with 10 wt % Catalyst

Dimethylamine (40% in water; 4.63 mL; 36.6 mmol; 2.5 equiv) was added to a flask which was then cooled in ice-water. Formic acid (88%; 1.34 mL; 30.7 mmol; 2.1 equiv) was added with a small exotherm. The cooling bath was removed and the mixture was allowed to warm to ambient temperature. 3-Hydroxypropionitrile (1.0 mL; 14.6 mmol) was added followed by 5% palladium on carbon (49.5% in water; 210 mg; 10 wt % based on hydroxypropionitrile). The mixture was heated to 50° C. and stirred and samples were removed and analyzed for conversion of 3-hydroxypropionitrile to 3-dimethylaminopropanol by $^1$H NMR: 1 h, 82% conversion; 2 h, 88% conversion; 3 h, 93% conversion; 8 h, 99% conversion, >99% selectivity to 3-dimethylaminopropanol.

TABLE 1

Rate effect of temperature

| | conversion | |
|---|---|---|
| Time (h) | Example 7 ambient temp | Example 8 50° C. |
| 1 | 72% | 82% |
| 2 | 80% | 88% |
| 3 | 87% | 93% |

Example 9

3-Diethylaminopropanol Using Water

Diethylamine (3.78 mL; 36.6 mmol; 2.5 equiv) and water (2.47 mL) were added to a 100-mL flask. Formic acid (96%; 1.21 mL; 30.7 mmol; 2.1 equiv) was added dropwise with a small exotherm. The cooling bath was removed and the mixture was allowed to warm to ambient temperature. 3-Hydroxypropionitrile (1.0 mL; 14.6 mmol) was added followed by 5% palladium on carbon (42.3% in water; 180 mg; 7.5 wt % based on hydroxypropionitrile). The mixture was stirred at RT and samples were removed and analyzed for conversion of 3-hydroxypropionitrile to 3-diethylaminopropanol by $^1$H NMR: 1 h, 39% conversion; 2 h, 52% conversion; 3 h, 60% conversion.
$^1$H NMR (DMSO-d$_6$): δ 3.42 (t, 2H, J=6.30 Hz); 2.46 (q, 4H, J=7.00 Hz); 2.45 (t, 2 h, J=6.80 Hz); 1.53 (m, 2H); 0.94 (t, 6H, J=7.10 Hz).

Example 10

3-Diethylaminopropanol with No Added Water

Diethylamine (3.78 mL; 36.6 mmol; 2.5 equiv) was added to a vial. Formic acid (96%; 1.21 mL; 30.7 mmol; 2.1 equiv) was added slowly dropwise with a small exotherm to afford a homogeneous mixture. 3-Hydroxypropionitrile (1.0 mL; 14.6 mmol) was added followed by 5% palladium on carbon (42.3% in water; 180 mg; 7.5 wt % based on hydroxypropionitrile). The mixture was stirred at RT and samples were removed and analyzed for conversion of 3-hydroxypropionitrile to 3-diethylaminopropanol by $^1$H NMR: 1 h, 6% conversion; 2 h, 7% conversion; 3 h, 9% conversion.

TABLE 2

Effect of water

| | conversion | |
|---|---|---|
| Time (h) | Example 9 with water | Example 10 no added water |
| 1 | 39% | 6% |
| 2 | 52% | 7% |
| 3 | 60% | 9% |

Example 11

3-Diethylaminopropanol with Twice the Amount of Water

Diethylamine (3.78 mL; 36.6 mmol; 2.5 equiv) and water (4.94 mL) were added to a vial. Formic acid (96%; 1.21 mL; 30.7 mmol; 2.1 equiv) was added slowly dropwise with a small exotherm to afford a homogeneous mixture. 3-Hydroxypropionitrile (1.0 mL; 14.6 mmol) was added followed by 5% palladium on carbon (42.3% in water; 180 mg; 7.5 wt % based on hydroxypropionitrile). The mixture was stirred at RT and samples were removed and analyzed for conversion of 3-hydroxypropionitrile to 3-diethylaminopropanol by $^1$H NMR: 1 h, 39% conversion; 2 h, 48% conversion; 3 h, 55% conversion.

Example 12

3-Dimethylaminopropanol Using Ammonium Formate as Hydrogen Donor

Dimethylamine (40% in water; 4.6 mL; 36.6 mmol; 2.5 equiv) as added to a 100-mL flask which then cooled in ice-water. Ammonium formate (1.94 g; 30.7 mmol; 2.1 equiv) was added and the mixture was stirred until it was homogeneous. 3-Hydroxypropionitrile (1.0 mL; 14.6 mmol) was added followed by 5% palladium on carbon (49.5% in water; 420 mg; 20 wt % based on hydroxypropionitrile). The mixture was stirred at RT and samples were removed and analyzed for conversion of 3-hydroxypropionitrile to 3-dimethylaminopropanol by $^1$H NMR: 4 h, 28% conversion; 50 h, 94% conversion, >98% selectivity to 3-dimethylaminopropanol.

Example 13

Dimethylpropylamine

Dimethylamine (40% in water; 4.15 mL; 32.8 mmol; 2.5 equiv) was added to a flask which was then cooled in ice-water. Formic acid (88%; 1.20 mL; 27.5 mmol; 2.1 equiv) was added with a small exotherm. The cooling bath was removed and the mixture was allowed to warm to ambient temperature. Propionitrile (1.0 mL; 0.72 g; 13.11 mmol) was added followed by 5% palladium on carbon (49.5% in water; 146 mg; 10 wt % based on propionitrile). The mixture was stirred at RT and samples were removed and analyzed for conversion of propionitrile to dimethylpropylamine by $^1$H NMR: 1 h, 41% conversion; 5 h, 73% conversion; 11 h, 83% conversion; 28 h, 95% conversion; 52 h, 98% conversion, >98% selectivity to dimethylpropylamine.

$^1$H NMR (DMSO-d$_6$) δ (ppm): 2.11 (t, 2H, J=7.2 Hz); 2.07 (s, 6H); 1.37 (m(6), 2H, J=7.5 Hz); 0.81 (t, 3H, J=7.4 Hz).

Example 14

N,N-Dimethylbenzylamine

Dimethylamine (40% in water; 3.07 mL; 24.2 mmol; 2.5 equiv) was added to a flask which was then cooled in ice-water. Formic acid (88%; 0.89 mL; 20.4 mmol; 2.1 equiv) was added with a small exotherm. The cooling bath was removed and the mixture was allowed to warm to ambient temperature. Benzonitrile (1.0 g; 9.7 mmol) was added followed by 5% palladium on carbon (49.5% in water; 202 mg; 10 wt % based on benzonitrile). The mixture was stirred at ambient temperature and samples were removed and analyzed for conversion of benzonitrile to N,N-dimethylbenzylamine by $^1$H NMR: 3 h, 30% conversion; 25 h, 39% conversion; 4 days, 53% conversion.

$^1$H NMR (DMSO-d$_6$) δ (ppm): 7.35-7.15 (m, 5H); 3.65 (s, 2H); 2.28 (s, 6H).

Although the disclosure describes embodiments having specific structural features and/or methodological acts, it is to be understood that the claims are not necessarily limited to the specific features or acts described. Rather, the specific features and acts illustrate some embodiments that fall within the scope of the claims of the disclosure.

What is claimed is:

1. A process for preparing amines comprising reacting at least one secondary amine, at least one hydrogen donor, and a nitrile of the general formula (2):

in the presence of a catalyst to obtain an amine of the general formula (1):

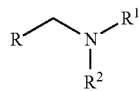

wherein R, R$^1$, and R$^2$ are independently selected from a group consisting of a C$_1$-C$_{22}$ alkyl, a C$_3$-C$_8$ cycloalkyl, a C$_6$-C$_{20}$ carbocyclic aryl, or a C$_1$-C$_{20}$ heterocyclic.

2. The process as recited in claim 1, wherein the C$_1$-C$_{22}$ alkyl is a hydrocarbon radical containing up to about 22 carbon atoms.

3. The process as recited in claim 2, wherein at least one hydrocarbon radical containing up to about 22 carbon atoms represented by R, R$^1$, and R$^2$ is substituted with one to three groups selected from a group consisting of a C$_1$-C$_6$ alkoxy, a C$_2$-C$_6$ alkoxycarbonyl, a C$_2$-C$_6$ alkanoyloxy, a hydroxyl, a carbocyclic aryl, and a heterocyclic.

4. The process as recited in claim 1, wherein the C$_6$-C$_{20}$ carbocyclic aryl is a phenyl, a naphthyl, or an anthracenyl.

5. The process as recited in claim 4, wherein the C$_6$-C$_{20}$ carbocyclic aryl is a phenyl, a naphthyl, or an anthracenyl substituted with one to three substituents selected from a group consisting of a C$_1$-C$_6$ alkyl, a substituted C$_1$-C$_6$ alkyl, a hydroxy, a C$_2$-C$_{10}$ dialkylamino, a C$_6$-C$_{10}$ aryl, a substituted C$_6$-C$_{10}$ aryl, a C$_1$-C$_6$ alkoxy, a carboxy, a C$_1$-C$_6$ alkanoyloxy, a C$_1$-C$_6$ alkylsulfonyl, a trifluoromethyl, a C$_2$-C$_6$ alkoxycarbonyl, a C$_2$-C$_6$ alkanoylamino and a O—R$^4$, a —SO$_2$—R$^4$, a —NHSO$_2$R$^4$ or —NHCO$_2$R$^4$, wherein R$^4$ is a phenyl, a naphthyl, or a phenyl or a naphthyl substituted with one to three groups selected from a C$_1$-C$_6$ alkyl, a C$_6$-C$_{10}$ aryl, or a C$_1$-C$_6$ alkoxy.

6. The process as recited in claim 1, wherein the C$_1$-C$_{20}$ heterocyclic is a 5- or 6-membered aromatic ring containing one to four heteroatoms selected from oxygen, sulfur and nitrogen.

7. The process as recited in claim 1, wherein the C$_1$-C$_{20}$ heterocyclic is a thienyl, a furyl, a pyrrolyl, an imidazolyl, a pyrazolyl, a thiazolyl, an isothiazolyl, an oxazolyl, an isoxazolyl, a triazolyl, a thiadiazolyl, an oxadiazolyl, a tetrazolyl, a pyridyl, a pyrimidyl, a benzoxazolyl, a benzothiazolyl, a benzimidazolyl, or an indolyl.

8. The process as recited in claim 1, wherein the C$_1$-C$_{20}$ heterocyclic is substituted with up to three groups from a group consisting of a C$_1$-C$_6$ alkyl, a C$_1$-C$_6$ alkoxy, a substituted C$_1$-C$_6$ alkyl, a hydroxy, a C$_2$-C$_{10}$ dialkylamino, an aryl, aryloxy, a C$_2$-C$_6$ alkoxycarbonyl, or a C$_2$-C$_6$ alkanoylamino.

9. The process as recited in claim 1, wherein the C$_3$-C$_8$ cycloalkyl is a carbocyclic hydrocarbon radical having three to eight carbon atoms which is substituted with one to three groups selected from a group consisting of a C$_1$-C$_6$ alkoxy, a C$_2$-C$_6$ alkoxycarbonyl, a C$_2$-C$_6$ alkanoyloxy, a hydroxy, a C$_2$-C$_{10}$ dialkylamino, a carbocyclic aryl, and a heterocyclic.

10. The process as recited in claim 1, wherein the process is carried out at a temperature from about −100° C. to about 200° C.

11. The process as recited in claim 1, wherein the catalyst is a Group VIII metal including one of palladium or platinum.

12. The process as recited in claim 1, wherein the process is carried out under air or nitrogen at atmospheric pressure.

* * * * *